United States Patent
Carle et al.

(10) Patent No.: US 10,561,601 B2
(45) Date of Patent: Feb. 18, 2020

(54) TOPICAL SKIN CARE FORMULATIONS COMPRISING BOTANICAL EXTRACTS

(71) Applicant: Mary Kay Inc., Addison, TX (US)

(72) Inventors: Tiffany Carle, Dallas, TX (US); David Gan, Southlake, TX (US); Michelle Hines, Hickory Creek, TX (US)

(73) Assignee: Mary Kay Inc., Addison, TX (US)

( * ) Notice: Subject to any disclaimer, the term of this patent is extended or adjusted under 35 U.S.C. 154(b) by 324 days.

(21) Appl. No.: 15/461,229

(22) Filed: Mar. 16, 2017

(65) Prior Publication Data

US 2017/0258707 A1    Sep. 14, 2017

Related U.S. Application Data

(63) Continuation of application No. 13/902,192, filed on May 24, 2013, now Pat. No. 9,629,793, which is a continuation of application No. 13/431,712, filed on Mar. 27, 2012, now Pat. No. 8,455,012, which is a continuation of application No. 12/855,391, filed on Aug. 12, 2010, now Pat. No. 8,173,184.

(60) Provisional application No. 61/234,115, filed on Aug. 14, 2009.

(51) Int. Cl.
| | |
|---|---|
| *A61K 8/97* | (2017.01) |
| *A61K 36/24* | (2006.01) |
| *A61K 36/62* | (2006.01) |
| *A61Q 19/08* | (2006.01) |
| *A61Q 19/00* | (2006.01) |
| *A61Q 19/10* | (2006.01) |

(52) U.S. Cl.
CPC ............... *A61K 8/97* (2013.01); *A61K 36/24* (2013.01); *A61K 36/62* (2013.01); *A61Q 19/00* (2013.01); *A61Q 19/007* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 6,296,859 | B1 | 10/2001 | Stoltz | 424/401 |
| 7,338,671 | B2 | 3/2008 | Golz-Berner | 424/725 |
| 2002/0012644 | A1 | 1/2002 | Chen | 424/70.1 |
| 2003/0152544 | A1 | 8/2003 | Chen | 424/74 |
| 2005/0196373 | A1 | 9/2005 | Chen | 424/74 |
| 2005/0255077 | A1 | 11/2005 | Golz-Berner et al. | 424/74 |
| 2006/0045849 | A1 | 3/2006 | Taghizadeh | 424/45 |
| 2006/0272105 | A1 | 12/2006 | Molenda et al. | 8/405 |
| 2007/0254021 | A1 | 11/2007 | Scimeca et al. | 424/450 |

FOREIGN PATENT DOCUMENTS

| | | | |
|---|---|---|---|
| EP | 1 728 502 | | 12/2006 |
| EP | 1 728 503 | | 12/2006 |
| JP | 08012586 A | * | 1/1996 |
| WO | WO 99/45899 | | 3/1999 |
| WO | WO 06/000708 | | 1/2006 |
| WO | WO 06/041526 | | 4/2006 |

OTHER PUBLICATIONS

Lima et al. "Correlation of Anti-Inflammatory Activity With Phenolic Content in the Leaves of *Syzygium cumini* (L.) Skeels (Myrtaceae)". Quim. Nova, vol. 30, No. 4, 860-864. (Year: 2007).*
Remington's. "Remington's Pharmaceutical Science 17th Edition". Gannaro, A (Ed.). pp. 1507-1509; 1512-1513. (Year: 1985).*
"*Syzygium* species" from "Purdue University Center for New Crops & Plants Products". Internet publication date: Jun. 24, 1997. [Retrieved from the Internet on: Apr. 1, 2019]. Retrieved from: <URL: https://www.hort.purdue.edu/newcrop/nexus/Syzygium_spp_nex.html>. (Year: 1997).*
Clark, J. "Use of Alcohols". Internet Publication Date: 2003 [Retrieved from the Internet on: Jan. 24, 2014]. Retrieved from: <URL:http://www.chemguide.co.uk!organicprops/alcohols/uses.html>.
James. "Master Organic Chemistry: Polar Protic? Polar Aprotic? Nonpolar? All about Solvents". Internet publication date: Apr. 27, 2012. [Retrieved from the Internet on: Jan. 24, 2014]. Retrieved from: <URL:http://www.masterorganicchemistry.com/2012/04/27/polar-protic-polar-aprotic-nonpolar-all-about-solvents/>.
Office Communication, issued in U.S. Appl. No. 12/855,391, dated Dec. 9, 2011.
Olshansky et al. Scientific American. vol. 92, No. 6 (2002) pp. 92-95.
Yaar et al. "Photoageing: mechanism, prevention and therapy". From Bench to Bedside. (2007) [Retrieved from the Internet on: Aug. 24, 2012]. Retrieved from: <http://www.laboratoriossilesia.com/upfiles/sibi/D1107903.pdf>.

* cited by examiner

*Primary Examiner* — Amy L Clark
(74) *Attorney, Agent, or Firm* — Norton Rose Fulbright US LLP

(57) ABSTRACT

Disclosed is method of treating skin by reducing TNF-a production in a person's skin in need of treatment, the method comprising topically applying a composition that includes an effective amount of an aqueous extract of *Syzygium moorei* leaf to the person's skin, wherein TNF-a production in the skin is reduced.

12 Claims, No Drawings

TOPICAL SKIN CARE FORMULATIONS COMPRISING BOTANICAL EXTRACTS

CROSS REFERENCE TO RELATED APPLICATIONS

This application is a continuation of U.S. application Ser. No. 13/902,192, filed May 24, 2013, which is a continuation of U.S. application Ser. No. 13/431,712, filed Mar. 27, 2012 (now issued as U.S. Pat. No. 8,455,012), which is a continuation of U.S. application Ser. No. 12/855,391, filed Aug. 12, 2010 (now issued as U.S. Pat. No. 8,173,184), which claims the benefit of U.S. Provisional Application No. 61/234,115, filed Aug. 14, 2009. The contents of the referenced applications are incorporated into the present application by reference.

BACKGROUND OF THE INVENTION

A. Field of the Invention

The present invention relates generally to compositions that include one or any combination of botanical extracts selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts. In particular aspects, the compositions include a *Nymphaea gigantea* extract, a *Syzygium moorei* extract, a *Cupaniopsis anacardioides* extract, a *Archidendron hendersonii* extract, a *Tristaniopsis laurina* extract, a *Brachychiton acerifolius* extract, or a *Stenocarpus sinuatus* extract, or any combination thereof. The compositions can be formulated as topical skin compositions, edible compositions, injectable compositions, oral compositions, hair care compositions, etc.

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

SUMMARY OF THE INVENTION

The present invention provides an effective alternative to existing skin active-ingredients that are used with topical application to keratinous tissue (e.g., skin, hair, nails, etc.). In this regard, the compositions of the present invention can include an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The compositions can be formulated as topical skin compositions, edible compositions, injectable compositions, oral compositions, hair care compositions, etc. In particular aspects, the compositions can include at least two, three, four, five, six, seven, eight, nine, ten, eleven, or all twelve of these extracts. The extract can be obtained from any part of the plant. Non-limiting examples include extracts obtain from the whole plant, leaves, stems, flowers, flower buds, bark, roots, fruit, seeds, seed pods, and any mixture of such parts. In certain aspects, the extract can be obtained from the whole fruit (e.g., fruit pulp and seeds), the whole plant (e.g., the entire plant is used to produce the extract), a particular part of the plant at the exclusion of another part (e.g., seed extract isolated from other parts of the plant), etc. The extract can be water-based, alcohol-based, oil-based, gel-based etc. The extract can be an aqueous extract. The solvent used to obtain the extract can include butylene glycol.

In certain embodiments, the compositions are formulated into topical skin or hair care compositions. The compositions can be cosmetic compositions. The compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydroalcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.).

The compositions of the present invention can include any desired amount of *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, or

*Tamarindus indica* extract, or any combination of such extracts. The amount of the extracts can individually or combined be from 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more, or any range derivable therein, by weight or volume of the extract or combination of extracts.

The compositions of the present invention can also be modified to have a desired oxygen radical absorbance capacity (ORAC) value. In certain non-limiting aspects, the compositions of the present invention or the plant extracts identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

In one aspect of the present invention, there is disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In another embodiment, there is disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; glycerin; butylene glycol; propylene glycol; phenoxyethanol; a chelating agent (e.g., EDTA, disodium EDTA, trisodium EDTA, EGTA, disodium EGTA, trisodium EGTA, citric acid, phosphoric acid, succinic acid, etc.); steareth-20; chlorhexidine diglunonate; potassium sorbate; and/or a preservative (e.g., methylparaben, propylparaben, butylparaben, ethylparaben, isobutylparaben, etc.). In particular aspects, the composition can further include any one of, any combination of, or all of the following additional ingredients: alcohol; denatured alcohol; glyceryl stearate; dimethicone; PEG-100 stearate; capryl glycol; triethanolamine; maltodextrin; sorbic acid; ethylene brassylate; methyl linalool; isobutyl methyl tetrahydropyranol; ethylhexylglycerin; and/or hexylene glycol. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In another aspect of the invention, there is disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; dimethicone; triethanolamine; phenonip; betaine; a chelating agent (e.g., EDTA, disodium EDTA, trisodium EDTA, EGTA, disodium EGTA, trisodium EGTA, citric acid, phosphoric acid, succinic acid, etc.); tocopheryl acetate; and/or prodew 400. In particular aspects, the composition can further include any one of, any combination of, or all of the following additional ingredients: propylene glycol; isododecane; polyacrylamide/C13-C14 isoparaffin/laureth 7 mixture; PEG-12 dimethicone; and/or ethylhexyl palmitate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In yet another embodiment there is disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; glycerin; pentylene glycol; capryl glycol; disodium EDTA; capric/caprylic triglyceride; shea butter; squalane; cetyl alcohol; dimethicone; ceramide II; stearic acid; a mixture of glyceryl stearate and PEG 100 stearate; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 7:1 to 9:1 based on the total weight of the composition. The ratio of glycerin to pentylene glycol can be from about 1:1 to about 2:1 based on the total weight of the composition. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

There is also disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; glycerin; capryl glycol; capryl glycol; disodium EDTA; petrolatum; squalane; cetyl alcohol; a mixture of glyceryl stearate and PEG 100 stearate; dimethicone; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 12:1 to 16:1 based on the total weight of the composition. The ratio of glycerin to pentylene glycol can be from about 0.5:1 to about 1.5:1 based on the total weight of the composition. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

Also disclosed is a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; xanthan gum; disodium EDTA; pentylene glycol; capryl glycol; acrylate C10-30 acrylate cross polymer; triethanolamine; PVP/hexadecene copolymer; C12-15 alkyl benzoate; sorbitan isostearate; or a sunscreen agent. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to C12-15 alkyl benzoate can be from about 2:1 to 3:1 based on the total weight of the composition. The ratio of water to pentylene glycol can be from about 9:1 to about 11:1 based on the total weight of the composition. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In yet another embodiment, there is disclosed a topical skin care composition that includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination of such extracts, in combination with any one of, any combination of, or all of the following ingredients: water; disodium EDTA; citric acid; pentylene glycol; capryl glycol; sodium cocoamphodiacetate; or sodium methyl cocoyl taurate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to pentylene glycol can be from about 12:1 to 14:1 based on the total weight of the composition. The ratio of water to sodium cocoamphodiacetate can be from about 8:1 to about 11:1 based on the total weight of the composition. The ratio of water to sodium methyl cocoyl taurate can be from about 2:1 to about 4:1 based on the total weight of the composition. The ratio of sodium methyl cocoyl taurate to sodium cocoamphodiacetate can be from about 2:1 to about 4:1 based on the total weight of the composition. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In one embodiment of the present invention there is disclosed a method of reducing the appearance of symptoms associated with erythema (e.g., erythemic skin, sensitive skin, inflamed skin) comprising topically applying a composition to erythemic, sensitive, or inflamed skin wherein the composition includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof and a dermatologically acceptable vehicle, wherein topical application of the composition to erythemic, sensitive, or inflamed skin reduces the appearance of symptoms associated with erythema, sensitive skin, or inflamed skin. In particular aspects, the composition includes *Nymphaea gigantea* extract. Further, the compositions described throughout the specification and claims can be used with this method. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

Also disclosed is a method of treating erythema comprising topically applying a composition to erythemic skin, sensitive skin, or inflamed skin, wherein the composition includes: an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof; and a dermatologically acceptable vehicle, wherein topical application of the composition to erythemic skin treats erythema, sensitive skin, or inflamed skin. In particular aspects, the composition includes *Nymphaea gigantea* extract. Further, the compositions described throughout the specification and claims can be used with this method. Erythema can be caused by skin sunburn, electrical treatments of skin, skin burns, contact allergies, systemic allergies, skin toxicity, exercise, insect stings, bacterial infection, viral infection, fungal infection, protozoa infection, massage, windburn, etc. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In still another aspect of the present invention there is disclosed a method of treating dry, flaky, or itchy skin or reducing the appearance of uneven skin tone comprising topically applying a composition to dry, flaky, or itchy skin or to skin having an uneven skin tone, wherein the composition includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof; and a dermatologically acceptable vehicle. In particular aspects, the composition includes *Nymphaea gigantea* extract. Further, the compositions described throughout the specification and claims can be used with this method. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

Also disclosed is a method of reducing the appearance of fine lines or wrinkles comprising topically applying a composition to skin having fine lines or wrinkles, wherein the composition includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof; and a dermatologically acceptable vehicle, wherein topical application of the composition to fine lines or wrinkles reduces the appearance of the fine lines or wrinkles. In particular aspects, the composition includes *Nymphaea gigantea* extract. Further, the compositions described throughout the specification and claims can be used with this method. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In one embodiment of the present invention there is disclosed a method of reducing pain associated with erythema, sensitive skin, or inflamed skin, comprising topically applying a composition to erythemic, sensitive, or inflamed skin wherein the composition includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof; and a dermatologically acceptable vehicle, wherein topical application of the composition to erythemic, sensitive, or inflamed skin reduces the pain associated with erythema, sensitive skin, or inflamed skin. In particular aspects, the composition includes *Nymphaea gigantea* extract. Further, the compositions described throughout the specification and claims can be used with this method. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In another embodiment there is disclosed a method of treating or preventing a skin condition comprising topically applying a composition to skin having a skin condition, wherein the composition includes an extract selected from the group consisting of: *Nymphaea gigantea* extract; *Syzygium moorei* extract; *Cupaniopsis anacardioides* extract; *Archidendron hendersonii* extract; *Tristaniopsis laurina* extract; *Brachychiton acerifolius* extract; *Stenocarpus sinuatus* extract; *Alphitonia excelsa* extract; *Eucalyptus coolabah* extract; *Plumeria alba* extract; *Cocos nucifera* extract; and *Tamarindus indica* extract; and any combination thereof; and a dermatologically acceptable vehicle, wherein topical application of the composition to the skin condition treats the skin condition. In particular aspects, the composition includes *Nymphaea gigantea* extract. Further, the compositions described throughout the specification and claims can be used with this method. Non-limiting examples of skin conditions include dry skin, itchy skin, inflamed skin, erythema, sensitive skin, pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin). In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment.

In yet another aspect of the present invention there is disclosed a method of treating or preventing a wide variety of diseases comprising administering to a patient in need of treatment a composition comprising *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, and/or *Tamarindus indica* extract, or any combination of said extracts (e.g., 2, 3, 4, 5, 6, 7, 8, 9, 10, or 11 of the aforementioned extracts), or all of said extracts. The composition can be formulated as a topical composition, an ingestible composition, an injectible composition, an aerosolized composition, etc. Non-limiting examples of diseases that can be treated or prevented with such compositions include AIDS, autoimmune diseases (e.g., rheumatoid arthritis, multiple sclerosis, diabetes—insulin-dependent and non-independent, systemic lupus erythematosus and Graves disease), cancer (e.g., malignant, benign, metastatic, precancer), cardiovascular diseases (e.g., heart disease or coronary artery disease, stroke—ischemic and hemorrhagic, and rheumatic heart disease), diseases of the nervous system, and infection by pathogenic microorganisms (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis), inflammation (e.g., allergy, asthma), prion diseases (e.g., CJD, kuru, GSS, FFI), obesity, etc. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In certain aspects, there is disclosed an aqueous extract of *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, and/or *Tamarindus indica* extract or any combination thereof. The aqueous extract can include butylene glycol. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

Also disclosed is a composition comprising an extract of an extract of *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, and/or *Tamarindus indica* extract, or any combination thereof. The composition can be an edible composition. The composition can take the form of a pill, liquid gel cap, or tablet. The composition can be an injectable solution (e.g., for intravenous delivery). The composition can be in the form of a neutraceutical. The extract can be an aqueous extract. The aqueous extract can include butylene glycol. In particular embodiments, the extract is *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract, or a combination thereof. The extract can be an aqueous extract. The solvent used to obtain the extract can include butylene glycol.

In a further aspect, there is disclosed a blend of *Cupaniopsis anacardioides* leaf, *Syzygium mooreii* leaf, and *Archidendron hendersonii* flower extracts. The extracts can each be aqueous extracts. Such aqueous extracts can include butylene glycol. The blend can be placed into any one of the compositions disclosed throughout this specification and can be used in any one of the methods disclosed throughout this specification.

In still another aspect, there is disclosed a blend of *Nymphaea gigantea* flower, *Tristaniopsis laurina* leaf, and *Eucalyptus coolabah* leaf extracts. The extracts can each be aqueous extracts. Such aqueous extracts can include butylene glycol. The blend can be placed into any one of the compositions disclosed throughout this specification and can be used in any one of the methods disclosed throughout this specification.

In yet another embodiment there is disclosed a blend of *Plumeria alba* flower, *Cocos nucifera* milk, and *Tamarindus indicia* leaf extracts. The extracts can each be aqueous extracts. Such aqueous extracts can include butylene glycol. The blend can be placed into any one of the compositions disclosed throughout this specification and can be used in any one of the methods disclosed throughout this specification.

A further aspect includes a blend of *Brachychiton acerifolius* leaf, *Stenocarpus sinuatus* leaf, and *Alphitonia excelsa* leaf extracts. The extracts can each be aqueous extracts. Such aqueous extracts can include butylene glycol. The blend can be placed into any one of the compositions disclosed throughout this specification and can be used in any one of the methods disclosed throughout this specification.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, tablets, gel capsules, injectible solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of compositions and ingredients currently used to treat aged skin, environmentally-damaged skin, uneven skin tone, and other skin conditions. In one non-limiting embodiment, the compositions of the present invention can be used to treat irritation of the skin and to improve the skin's visual appearance, physiological functions, clinical properties, or biophysical properties by providing a composition of the present invention to an area of the skin that needs such treatment. As noted throughout this specification, the compositions can include any one of *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, or *Tamarindus indica* extract, or any combination of such extracts. These and other non-limiting aspects of the present invention are described in further detail below.

A. Extracts

*Nymphaea gigantea*, also known as the giant water lily, can be found in the tropical and subtropical regions of Australia. *Nymphaea gigantea* has large (up to 25 cm) blue-white flowers that emerge from the water and large circular leaves that grow up to 75 cm in diameter. This plant also produces seeds.

*Syzygium moorei*, also known as the rose apple, coolamon, robby, durobby, and watermelon tree, is a tree that can be found in the sub tropical regions of Australia. It has green foliage and can produce flowers and fruit on mature stems and woody trunks. Seeds can also be produced by this tree.

*Cupaniopsis anachardiodes*, also known as tuckeroo, carrot wood, cashew leaf cupania, brush deal, cupania tree, *Cupaniopsis*, yowarro, or *Cupaniopsis*, is a small tree that can be found in Australia, Indonesia, and New Guinea. It has green foliage and can produce greenish-yellow flowers which are followed by fruit and orange seed pods with seeds.

*Archidendron hendersonii*, also known as white lace flower or tulip siris, is a tree that can be found in the coastal regions of New South Wales and Queensland Australia. It has green foliage and can produce fluffy creamy-white flowers and woody orange seed pods that have black seeds.

*Tristaniopsis laurina*, also known as the water gum or Kanooka tree, is a tree that has a smooth, creamy-brown trunk and green foliage. It can produce yellow flowers. It can be found on the eastern coastline of Australia.

*Brachychiton acerifolius*, also known as the flame tree or illiawarra flame tree, can be found in the subtropical regions on the east coast of Australia. Its has green foliage and can produce bright red bell-shaped flowers. It can also produce yellow seeds and pod-like fruits that can reach 10 cm in length.

*Stenocarpus sinuatus*, also known as the Queensland Firewheel tree, is a tree that can be found in the New South Wales and Queensland regions of Australia. It is an evergreen tree that can produce red wagon wheel shaped flowers. It also produces follicle shaped fruit that can reach up to 10 cm in length. Inside the fruit are thin seeds.

*Alphitonia excelsa*, also known as the Red Ash or Soap Tree, is a tree that can be found in the New South Wales, Queensland, and Northern Territory regions of Australia. It has green foliage and can produce silvery fine flower buds which are followed by purplish-black fruits having a red pulp and seeds.

*Eucalyptus coolabah*, also known as collibah or *Coolabah*, is a *Eucalyptus* tree that can be found in the Northern Territory and New South Wales regions of Australia. It has elongated greenish blue foliage and can produce seed pods that include seeds.

*Plumeria alba*, also known as White Frangipani or Nosegay Tree, is a tree that can be found throughout Australia. It is a tree that has green foliage and can produce a white and yellow flower. It has green palm leaves and can produce flowers and coconuts.

*Cocos nucifera*, also known as the Coconut Palm, is a palm tree that can be found throughout the tropical regions of the world. It has green palm leaves and can produce flowers and coconuts.

*Tamarindus indica*, also known as Tamarind, is a tree that can be found throughout the tropical regions of the world. It has green foliage and can produce yellow flowers and reddish brown pods with seeds.

The inventors have discovered that each of the extracts identified above have several biological activities, which can be beneficial to skin. Non-limiting examples of some of these biological activities include inhibition of inflammatory mediators, which can reduce skin erythema, skin redness, or skin irritation. Compositions comprising the extracts can also be used to alleviate pain associated with sensitive or inflamed skin. The extracts can be obtained from any and all parts of the plant (e.g., leaves, stems, bark, roots, fruit, flowers or flower buds, seeds, seed pods, the entire plant, etc.). In particular aspects, the extract is from *Nymphaea gigantea* flower, *Syzygium moorei* leaf, *Cupaniopsis anacardioides* leaf, *Archidendron hendersonii* flower, *Tristaniopsis laurina* leaf, *Brachychiton acerifolius* leaf, *Stenocarpus sinuatus* leaf, *Alphitonia excelsa* leaf, *Eucalyptus coolabah* leaf, *Plumeria alba* flower, *Cocos nucifera* milk, or *Tamarindus indica* leaf extract. The extract can be aqueous. The extract can include butylene glycol. Butylene glycol can be used as a solvent to prepare the extract.

A person of ordinary skill in the art would be able to isolate extracts from each of the above mentioned plants from parts of these plant by using any suitable method known in the art. In one non-limiting example, such plants (or any part of the plants—e.g., leaves, stems, bark, roots, fruit, flowers or flower buds, seeds, seed pods, the entire plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, fruit, seeds, seed pods, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc. In particular embodiments, butylene glycol extraction works well (see Examples).

B. Compositions of the Present Invention

1. Combinations and Amounts of Ingredients

It is contemplated that the compositions of the present invention can include any one of *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, or *Tamarindus indica* extract, or any combination of such extracts. The compositions can also include additional ingredients described throughout this specification. The concentrations of the plant extracts and/or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the plant extracts identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the plant extracts and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. Nos. 6,387,398; 6,203,802; 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

3. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), 12$^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) water-proofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Sunscreen Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

ii. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea *Officinalis* extract, aluminum starch octenylsuccinate, aluminum stearate, apricot (*Prunus armeniaca*) kernel oil, arginine, arginine aspartate, *Arnica montana* extract, ascorbic acid, ascorbyl palmitate, aspartic acid, avocado (*Persea gratissima*) oil, barium sulfate, barrier sphingolipids, butyl alcohol, beeswax, behenyl alcohol, beta-sitosterol, BHT, birch (*Betula alba*) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *Eucalyptus globulus* oil, evening primrose (*Oenothera biennis*) oil, fatty acids, fructose, gelatin, geranium *Maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia *Ternifolia* nut oil, magnesium stearate, magnesium sulfate, maltitol, *Matricaria* (*Chamomilla recutita*) oil, methyl glucose sesquistearate, methylsilanol PCA, microcrystalline wax, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *Sclerotium* gum, sodium carboxymethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

C. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

An aqueous extract of *Nymphaea gigantea* flower in butylene glycol was used to obtain the data in Table I. Butylene glycol was used as the extraction solvent.

TABLE I

| Extract | AO Assay | Elastase Assay | TNF-α Assay | MMP1 Assay |
|---|---|---|---|---|
| *Nymphaea gigantea* flower extract* | — | — | exhibited inhibition of TNF-α activity | exhibited inhibition of MMP1 activity |

*Extract was obtained from Southern Cross Botanicals Pty. Ltd., Knockrow, New South Wales (Australia).

Antioxidant (AO) Assay:

Anti-Oxidant capacity kit #709001 from Cayman Chemical (Ann Arbor, Mich. USA) was used as an in vitro bioassay to measure the total anti-oxidant capacity of the extracts identified in Table 1. The protocol was followed according to manufacturer recommendations. The assay relied on antioxidants in the sample to inhibit the oxidation of ABTS® (2,2'-azino-di-[3-ethylbenzthiazoline sulphonate]) to ABTS®•+ by metmyoglobin. The capacity of the antioxidants in the sample to prevent ABTS oxidation was compared with that Trolox, a water-soluble tocopherol analogue, and was quantified as a molar Trolox equivalent. Extracts that have antioxidant capabilities can protect a target (e.g., skin, food, etc.) from oxidative damage from free-radicals, reactive oxygen species, UV radiation, etc.

Elastase Assay:

EnzChek® Elastase Assay (Kit# E-12056) from Molecular Probes (Eugene, Oreg. USA) was used as an in vitro enzyme inhibition assay for measuring inhibition of elastase activity for the extracts identified in Table 1. The EnzChek kit contains soluble bovine neck ligament elastin that has been labeled with dye such that the conjugate's fluorescence is quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, is used as a selective, collective inhibitor of elastase when utilizing the EnzChek Elastase Assay Kit for screening for elastase inhibitors. Extracts that have the ability to inhibit elastase activity can increase (or prevent the loss of) elastin present in the skin. This can firm skin, tone skin, reduce the appearance of fine lines or wrinkles, etc.

Tumor Necrosis Factor Alpha (TNF-α) Assay:

The anti-irritant capability of the extracts identified in Table 1 were evaluated by measuring inhibition of TNF-α release by primary human keratinocytes in response to stress. Primary human keratinocytes were induced to release TNF-α, a pleiotropic cytokine that plays a central role in inflammation, in the presence or absence of the extract. TNF-α secretion was quantified using R&D Systems (Minneapolis, Minn. USA) TNF-α Enzyme-linked Immunosorbant Assay #DTA00C according to manufacturer instructions. This sandwich immunoassay technique used color development to quantify the amount of TNF-α present in the cellular supernatant. Color developed in proportion to the amount of TNF-α and was detected at 450 nm using a microplate reader. Data were calculated as % inhibition of the untreated controls. Negative values demonstrated the ability of test ingredients to inhibit the production of TNF-α compared to controls. Extracts that have the ability to inhibit TNF-α activity can reduce or prevent the deleterious effects caused by the inflammatory pathway (e.g., reduce skin inflammation, treat or prevent inflammatory diseases, etc.).

Matrix Metalloproteinase Enzyme Activity (MMP1) Assay:

Collagen, an extracellular matrix protein produced in healthy skin, is degraded by the enzyme collagenase. The Invitrogen (Carlsbad, Calif. USA) EnzChek Gelatinase/Collagenase Assay Kit #E-12055 was used to quantify the capability of the extracts identified in Table 1 to inhibit the activity of MMP1 (Collagenase). The protocol was followed according to manufacturer recommendations. The assay contained a soluble gelatin substrate labeled with a fluorescent dye such that the conjugate's fluorescence was quenched. Once cleaved by collagenase or other proteases, the substrate yielded highly fluorescent fragments measured using a microplate reader. The non-fluorescent substrate was incubated with MMP1 in the presence or absence of the extract. The ability of the extracts to prevent substrate cleavage was quantified and compared to positive controls. Extracts that have the ability to inhibit MMP1 activity can increase (or prevent the loss of) collagen present in the skin. This can firm skin, tone skin, reduce the appearance of fine lines or wrinkles, etc.

Example 2

An aqueous extract of *Tristaniopsis laurina* leaf in butylene glycol was used to obtain the data in Table II. Butylene glycol was used as the extraction solvent.

TABLE II*

| Extract | AO Assay | Elastase Assay | TNF-α Assay | MMP1 Assay |
|---|---|---|---|---|
| *Tristaniopsis laurina* leaf extract** | — | exhibited inhibition of elastase activity | exhibited inhibition of TNF-α activity | — |

*Data obtained by using the same assays described in Example 1.
**Extract was obtained from Southern Cross Botanicals Pty. Ltd., Knockrow, New South Wales (Australia).

Example 3

A blend of aqueous extracts of *Cupaniopsis anacardiodes* leaf, *Syzygium mooreii* leaf, and *Archidendron hendersonii* flower in butylene glycol were used to obtain the data in Table III. Butylene glycol was used as the extraction solvent.

TABLE III*

| Extract | AO Assay | Elastase Assay | TNF-α Assay | MMP1 Assay |
|---|---|---|---|---|
| Blend of *Cupaniopsis anacardiodes* leaf, *Syzygium mooreii* leaf, and *Archidendron hendersonii* flower extracts** | exhibited antioxidant activity | exhibited inhibition of elastase activity | exhibited inhibition of TNF-α activity | exhibited inhibition of MMP1 activity |

*Data obtained by using the same assays described in Example 1.
**Blend was obtained from Southern Cross Botanicals Pty. Ltd., Knockrow, New South Wales (Australia).

Example 4

A blend of aqueous extracts of *Nymphaea gigantea* flower, *Tristaniopsis laurina* leaf, and *Eucalyptus coolabah* leaf in butylene glycol were used to obtain the data in Table IV.

TABLE IV*

| Extract | AO Assay | Elastase Assay | TNF-α Assay | MMP1 Assay |
|---|---|---|---|---|
| Blend of *Nymphaea gigantea* flower, *Tristaniopsis laurina* leaf, and *Eucalyptus coolabah* leaf extracts** | — | exhibited inhibition of elastase activity | exhibited inhibition of TNF-α activity | exhibited inhibition of MMP1 activity |

*Data obtained by using the same assays described in Example 1.
**Blend was obtained from Southern Cross Botanicals Pty. Ltd., Knockrow, New South Wales (Australia).

Example 5

A blend of aqueous extracts of *Plumeria alba* flower, *Cocos nucifera* milk, and *Tamarindus indicia* leaf extracts in butylene glycol were used to obtain the data in Table V. Butylene glycol was used as the extraction solvent.

TABLE V*

| Extract | AO Assay | Elastase Assay | TNF-α Assay | MMP1 Assay |
|---|---|---|---|---|
| Blend of *Plumeria alba* flower, *Cocos nucifera* milk, and *Tamarindus indicia* leaf extracts** | — | exhibited inhibition of elastase activity | exhibited inhibition of TNF-α activity | exhibited inhibition of MMP1 activity |

*Data obtained by using the same assays described in Example 1.
**Blend was obtained from Southern Cross Botanicals Pty. Ltd., Knockrow, New South Wales (Australia).

extracts in butylene glycol were used to obtain the data in Table VI. Butylene glycol was used as the extraction solvent.

TABLE VI*

| Extract | AO Assay | Elastase Assay | TNF-α Assay | MMP1 Assay |
|---|---|---|---|---|
| *Brachychiton acerifolius* leaf, *Stenocarpus sinuatus* leaf, and *Alphitonia excelsa* leaf extracts** | — | — | exhibited inhibition of TNF-α activity | exhibited inhibition of MMP1 activity |

*Data obtained by using the same assays described in Example 1.
**Blend was obtained from Southern Cross Botanicals Pty. Ltd., Knockrow, New South Wales (Australia).

Example 7

Each extract listed in Table VII is an aqueous extract in butylene glycol. Butylene glycol was used as the extraction solvent. The data in Table VII was obtained by using the same assays described in Example 1. Each extract was obtained from Southern Cross Botanicals Pty. Ltd., Knockrow, New South Wales (Australia).

TABLE VII

| Extract | AO Assay | Elastase Assay | TNF-α Assay | MMP1 Assay |
|---|---|---|---|---|
| *Syzygium moorei* leaf | exhibited some antioxidant activity | — | exhibited inhibition of TNF-α activity | — |
| *Cupaniopsis anacardioides* leaf | exhibited antioxidant activity | exhibited inhibition of elastase activity | exhibited inhibition of TNF-α activity | exhibited inhibition of MMP1 activity |
| *Archidendron hendersonii* flower | — | exhibited some inhibition of elastase activity | exhibited inhibition of TNF-α activity | — |
| *Eucalyptus coolabah* leaf | — | exhibited inhibition of elastase activity | exhibited inhibition of TNF-α activity | — |
| *Brachychiton acerifolius* leaf | — | — | exhibited inhibition of TNF-α activity | exhibited inhibition of MMP1 activity |
| *Stenocarpus sinuatus* leaf | — | — | exhibited inhibition of TNF-α activity | — |
| *Alphitonia excelsa* leaf | — | — | exhibited inhibition of TNF-α activity | — |
| *Plumeria alba* flower | — | exhibited some inhibition of elastase activity | exhibited inhibition of TNF-α activity | — |
| *Cocos nucifera* milk | — | exhibited inhibition of elastase activity | exhibited inhibition of TNF-α activity | exhibited inhibition of MMP1 activity |
| *Tamarindus indica* leaf | — | exhibited inhibition of elastase activity | exhibited inhibition of TNF-α activity | exhibited inhibition of MMP1 activity |

Example 6

A blend of aqueous extracts of *Brachychiton acerifolius* leaf, *Stenocarpus sinuatus* leaf, and *Alphitonia excelsa* leaf Example 8

Tables VIII and IX describe generic skin testing formulations in which a skin active ingredient can be incorporated into to determine the types of skin benefits that can be attributed to the skin active ingredient. These formulations are prepared in such a manner that any resulting skin benefit from topical application of the formula to skin can be directly attributed to the skin active ingredient being tested. In the context of the present invention, the skin active ingredient that can be tested can be any of the extracts identified in Tables and any combination thereof. Further, any portion of the plant can be used for testing (e.g., root, stem, leaf, flower, flower bulb, bark, fruit, seed, seed pod, whole plant etc.). It should be recognized that other standard testing vehicles can also be used to determine the skin benefit properties of extracts obtained from the plant extracts and that the following formulations are non-limiting testing vehicles.

TABLE VIII*

| Ingredient | % Concentration (by weight) |
|---|---|
| Phase A | |
| Water | 84.80 |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Skin Active Ingredient | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water.

TABLE IX*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |

TABLE IX*-continued

| Ingredient | % Concentration (by weight) |
|---|---|
| Phase C** | |
| Skin Active Ingredient | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water.

The formulations represented in Table X-XV are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition.

Table X includes a non-limiting example of a composition of the present invention. The composition can be formulated into an emulsion (e.g., o/w, w/o, o/w/o, w/o/w, etc.) and the additional ingredients identified throughout the specification can be included into the Table X composition (e.g., by adjusting the water content of composition). Further, the concentration ranges of the ingredients identified in Table X can vary depending on a desired formulation (e.g., cream, lotion, moisturizer cleanser, etc.).

TABLE X

| Ingredient | % Concentration (by weight) |
|---|---|
| Water | q.s. |
| Skin active ingredient* | 0.1% to 10% |
| Glycerin | 3 to 40% |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Diglunonate | 0.0001 to 10% |
| Potassium Sorbate | 0.0001 to 10% |
| Preservative** | 0.0001 to 2% |
| TOTAL | 100 |

*Skin active ingredient can be any of the individual plant extracts identified throughout the specification or any combination of such extracts (e.g., Nymphaea gigantea extract, Syzygium moorei extract, Cupaniopsis anacardioides extract, Archidendron hendersonii extract, Tristaniopsis laurina extract, Brachychiton acerifolius extract, Stenocarpus sinuatus extract, Alphitonia excelsa extract, Eucalyptus coolabah extract, Plumeria alba extract, Cocos nucifera extract, or Tamarindus indica extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be Nymphaea gigantea extract, Syzygium moorei extract, Cupaniopsis anacardioides extract, Archidendron hendersonii extract, Tristaniopsis laurina extract, Brachychiton acerifolius extract, or Stenocarpus sinuatus extract, or any combination of such extracts. In even more particular aspects, the extract can be a Nymphaea gigantea extract.
**Any preservative can be used identified in the specification or those known in the art.

Table XI includes a non-limiting example of a composition of the present invention. The composition can be formulated into an emulsion (e.g., o/w, w/o, o/w/o, w/o/w, etc.) and the additional ingredients identified throughout the specification can be included into the Table XI composition (e.g., by adjusting the water content of composition). Further, the concentration ranges of the ingredients identified in Table XI can vary depending on a desired formulation (e.g., cream, lotion, moisturizer cleanser, etc.).

TABLE XI

| Ingredient | % Concentration (by weight) |
| --- | --- |
| Water | q.s. |
| Skin active ingredient* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |
| Prodew 400 | 0.0001 to 10% |
| Preservative** | 0.0001 to 2% |
| TOTAL | 100 |

*Skin active ingredient can be any of the individual plant extracts identified throughout the specification or any combination of such extracts (e.g., Nymphaea gigantea extract, Syzygium moorei extract, Cupaniopsis anacardioides extract, Archidendron hendersonii extract, Tristaniopsis laurina extract, Brachychiton acerifolius extract, Stenocarpus sinuatus extract, Alphitonia excelsa extract, Eucalyptus coolabah extract, Plumeria alba extract, Cocos nucifera extract, or Tamarindus indica extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be Nymphaea gigantea extract, Syzygium moorei extract, Cupaniopsis anacardioides extract, Archidendron hendersonii extract, Tristaniopsis laurina extract, Brachychiton acerifolius extract, or Stenocarpus sinuatus extract, or any combination of such extracts. In even more particular aspects, the extract can be a Nymphaea gigantea extract.
**Any preservative can be used identified in the specification or those known in the art.

Table XII includes a non-limiting example of a composition of the present invention. The composition can be formulated into an emulsion (e.g., o/w, w/o, o/w/o, w/o/w, etc.) and the additional ingredients identified throughout the specification can be included into the Table XII composition (e.g., by adjusting the water content of composition). Further, the concentration ranges of the ingredients identified in Table XII can vary depending on a desired formulation (e.g., cream, lotion, moisturizer cleanser, etc.). In particular embodiments, the Table XII composition can be a moisturizer.

TABLE XII

| Ingredient | % Concentration (by weight) |
| --- | --- |
| Water | q.s. |
| Skin active ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Capric/Caprylic Triglyceride | 0.0001 to 10% |
| Lipex 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| Arlacel 165 | 0.0001 to 10% |
| Simulgel 600 | 0.0001 to 10% |
| TOTAL | 100 |

*Skin active ingredient can be any of the individual plant extracts identified throughout the specification or any combination of such extracts (e.g., Nymphaea gigantea extract, Syzygium moorei extract, Cupaniopsis anacardioides extract, Archidendron hendersonii extract, Tristaniopsis laurina extract, Brachychiton acerifolius extract, Stenocarpus sinuatus extract, Alphitonia excelsa extract, Eucalyptus coolabah extract, Plumeria alba extract, Cocos nucifera extract, or Tamarindus indica extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be Nymphaea gigantea extract, Syzygium moorei extract, Cupaniopsis anacardioides extract, Archidendron hendersonii extract, Tristaniopsis laurina extract, Brachychiton acerifolius extract, or Stenocarpus sinuatus extract, or any combination of such extracts. In even more particular aspects, the extract can be a Nymphaea gigantea extract.

Table XIII includes a non-limiting example of a composition of the present invention. The composition can be formulated into an emulsion (e.g., o/w, w/o, o/w/o, w/o/w, etc.) and the additional ingredients identified throughout the specification can be included into the Table XIII composition (e.g., by adjusting the water content of composition). Further, the concentration ranges of the ingredients identified in Table XIII can vary depending on a desired formulation (e.g., cream, lotion, moisturizer cleanser, etc.). In particular embodiments, the Table XIII composition can be a moisturizer.

TABLE XIII

| Ingredient | % Concentration (by weight) |
| --- | --- |
| Water | q.s. |
| Skin active ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| Arlacel 165 | 0.0001 to 10% |
| Dimethicone | 0.0001 to 10% |
| Simulgel 600 | 0.0001 to 10% |
| TOTAL | 100 |

*Skin active ingredient can be any of the individual plant extracts identified throughout the specification or any combination of such extracts (e.g., Nymphaea gigantea extract, Syzygium moorei extract, Cupaniopsis anacardioides extract, Archidendron hendersonii extract, Tristaniopsis laurina extract, Brachychiton acerifolius extract, Stenocarpus sinuatus extract, Alphitonia excelsa extract, Eucalyptus coolabah extract, Plumeria alba extract, Cocos nucifera extract, or Tamarindus indica extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be Nymphaea gigantea extract, Syzygium moorei extract, Cupaniopsis anacardioides extract, Archidendron hendersonii extract, Tristaniopsis laurina extract, Brachychiton acerifolius extract, or Stenocarpus sinuatus extract, or any combination of such extracts. In even more particular aspects, the extract can be a Nymphaea gigantea extract.

Table XIV includes a non-limiting example of a composition of the present invention. The composition can be formulated into an emulsion (e.g., o/w, w/o, o/w/o, w/o/w, etc.) and the additional ingredients identified throughout the specification can be included into the Table XIV composition (e.g., by adjusting the water content of composition). Further, the concentration ranges of the ingredients identified in Table XIV can vary depending on a desired formulation (e.g., cream, lotion, moisturizer cleanser, etc.). In particular embodiments, the Table XIV composition can be a sunscreen lotion.

TABLE XIV

| Ingredient | % Concentration (by weight) |
| --- | --- |
| Water | q.s. |
| Skin active ingredient* | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| Pemulen TR-1 | 0.0001 to 10% |
| Triethanolamine | 0.0001 to 10% |
| PVP/Hexadecene Copolymer | 0.0001 to 10% |
| Finsolv TN | 10 to 30% |

TABLE XIV-continued

| Ingredient | % Concentration (by weight) |
| --- | --- |
| Sorbitan Isostearate | 0.0001 to 10% |
| Sunscreen Ingredient** | 2 to 25% |
| TOTAL | 100 |

*Skin active ingredient can be any of the individual plant extracts identified throughout the specification or any combination of such extracts (e.g., *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, or *Tamarindus indica* extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, or *Stenocarpus sinuatus* extract, or any combination of such extracts. In even more particular aspects, the extract can be a *Nymphaea gigantea* extract.
**Sunscreen ingredient can be any sunscreen ingredient, or combination of such ingredients, identified in the specification or known to those of ordinary skill in the art. In one embodiment, the sunscreen ingredient is a combination of zinc oxide and titanium dioxide.

Table XV includes a non-limiting example of a composition of the present invention. The additional ingredients identified throughout the specification can be included into the Table XV composition (e.g., by adjusting the water content of composition). Further, the concentration ranges of the ingredients identified in Table XV can vary depending on a desired formulation (e.g., cream, lotion, moisturizer cleanser, etc.). In particular embodiments, the Table XV composition can be a cleanser.

TABLE XV

| Ingredient | % Concentration (by weight) |
| --- | --- |
| Water | q.s. |
| Skin active ingredient* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| sodium methyl cocoyl taurate | 10 to 30% |
| sodium cocoamphodiacetate | 1 to 10% |
| TOTAL | 100 |

*Skin active ingredient can be any of the individual plant extracts identified throughout the specification or any combination of such extracts (e.g., *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, *Stenocarpus sinuatus* extract, *Alphitonia excelsa* extract, *Eucalyptus coolabah* extract, *Plumeria alba* extract, *Cocos nucifera* extract, or *Tamarindus indica* extract, or any combination of such extracts). Any portion of the plant can be used to create the skin-active extract (e.g., root, stem, leaf, flower, flower bulb, bark, fruit, seed, seed pod, whole plant etc.). In particular embodiments, the extract can be *Nymphaea gigantea* extract, *Syzygium moorei* extract, *Cupaniopsis anacardioides* extract, *Archidendron hendersonii* extract, *Tristaniopsis laurina* extract, *Brachychiton acerifolius* extract, or *Stenocarpus sinuatus* extract, or any combination of such extracts. In even more particular aspects, the extract can be a *Nymphaea gigantea* extract.

Example 9

Assays that can be Used to Test Compositions

The efficacy of compositions comprising the plant extracts identified throughout the specification, or a combination of such extracts (including, for example, the formulations identified in the above Tables), can be determined by methods known to those of ordinary skill in the art. The following are non-limiting assays that can be used in the context of the present invention. It should be recognized that other testing procedures can be used, including, for example, objective and subjective procedures.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Micro-texture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1 cm-1 at pH 6.0 and above 7).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.

U.S. Pat. No. 2,798,053
U.S. Pat. No. 3,755,560
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,411,744
U.S. Pat. No. 6,203,802
U.S. Pat. No. 6,387,398
U.S. Patent Publn. 2004/0109905
U.S. Patent Publn. 2005/0163880
Cao et al., *Free Radic. Biol. Med.*, 14:303-311, 1993.
CTFA International Cosmetic Ingredient Dictionary and Handbook, 12$^{th}$ Ed., 2008.
CTFA International Cosmetic Ingredient Dictionary, 4$^{th}$ Ed., pp 12 and 80, 1991.
Kreuter, *J. Microencapsulation*, 5:115-127, 1988.
*McCutcheon's Emulsifiers and Detergents*, North American Edition, 1986.
Packman and Gams, *J. Soc. Cos. Chem.*, 29:70-90, 1978.

The invention claimed is:

1. A method of treating skin by reducing TNF-$\alpha$ production in a person's skin in need of treatment, the method comprising topically applying a composition that includes an effective amount of an aqueous extract of *Syzygium moorei* leaf to the person's skin, wherein TNF-$\alpha$ production in the skin is reduced.

2. The method of claim 1, wherein the composition comprises 0.01% to 20% by weight of the aqueous extract of *Syzygium moorei* leaf.

3. The method of claim 1, wherein the composition further comprises a moisturizing agent or a humectant.

4. The method of claim 1, wherein the composition comprises at least 50% by weight of water.

5. The method of claim 1, wherein the aqueous extract of *Syzygium moorei* leaf further comprises butylene glycol.

6. The method of claim 1, wherein the composition is a gel.

7. The method of claim 1, wherein the composition is an emulsion.

8. The method of claim 1, wherein the composition is applied to erythemic skin.

9. The method of claim 1, wherein the composition is applied to sensitive skin.

10. The method of claim 1, wherein the composition is applied to inflamed skin.

11. The method of claim 1, wherein the composition is applied to dry, flaky, or itchy skin.

12. The method of claim 1, wherein the composition is applied to a fine line or a wrinkle.

* * * * *